(12) United States Patent
Zolotov

(10) Patent No.: US 8,231,659 B2
(45) Date of Patent: Jul. 31, 2012

(54) ANCHORING MECHANISM

(75) Inventor: Aleksandr G. Zolotov, Collierville, TN (US)

(73) Assignee: Warsaw Orthopedic, Warsaw, IN (US)

( * ) Notice: Subject to any disclaimer, the term of this patent is extended or adjusted under 35 U.S.C. 154(b) by 126 days.

(21) Appl. No.: 12/847,601

(22) Filed: Jul. 30, 2010

(65) Prior Publication Data
US 2012/0029572 A1 Feb. 2, 2012

(51) Int. Cl.
*A61B 17/70* (2006.01)
(52) U.S. Cl. ......................... 606/278; 606/279
(58) Field of Classification Search ................... 606/300, 606/305–308, 246–279
See application file for complete search history.

(56) References Cited

U.S. PATENT DOCUMENTS

| | | | | |
|---|---|---|---|---|
| 5,499,983 A * | 3/1996 | Hughes | | 606/267 |
| 5,507,746 A * | 4/1996 | Lin | | 606/264 |
| 5,716,356 A * | 2/1998 | Biedermann et al. | | 606/271 |
| 6,027,533 A * | 2/2000 | Olerud | | 623/16.11 |
| 7,285,121 B2 | 10/2007 | Braun et al. | | |
| 7,686,814 B2 | 3/2010 | Lim et al. | | |
| 2002/0007184 A1 | 1/2002 | Ogilvie et al. | | |
| 2007/0055239 A1 * | 3/2007 | Sweeney et al. | | 606/61 |
| 2008/0161858 A1 * | 7/2008 | Mahoney et al. | | 606/265 |
| 2008/0221620 A1 * | 9/2008 | Krause | | 606/255 |
| 2009/0062861 A1 * | 3/2009 | Frasier et al. | | 606/278 |

FOREIGN PATENT DOCUMENTS

WO 9952586 4/1999
WO 2010003139 1/2010

* cited by examiner

*Primary Examiner* — Eduardo C Robert
*Assistant Examiner* — Michelle C Eckman

(57) ABSTRACT

A system for anchoring at least a portion of material to a vertebral body is disclosed. The anchoring system comprises a base configured to affix to the vertebral body and configured to receive the at least a portion of material, and an anchoring mechanism configured to engage with the base and configured to anchor the at least a portion of material, wherein the mechanism comprises at least one elastic element configured to apply pressure to the at least a portion of material so as to anchor the at least a portion of material to the base. Also, a method for attaching at least a portion of material to bone is disclosed.

20 Claims, 10 Drawing Sheets

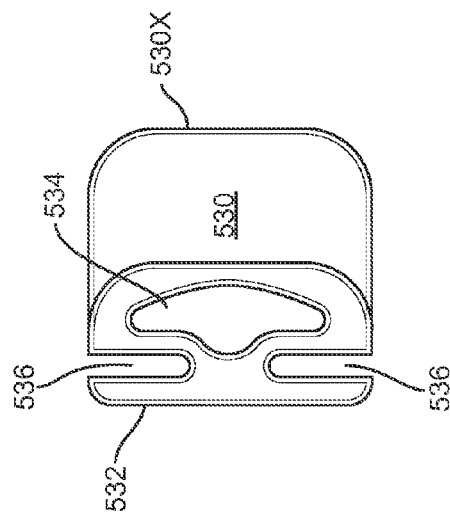
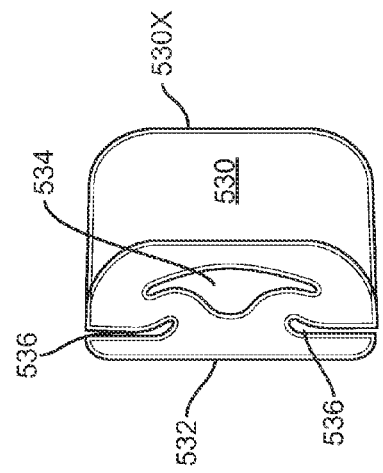
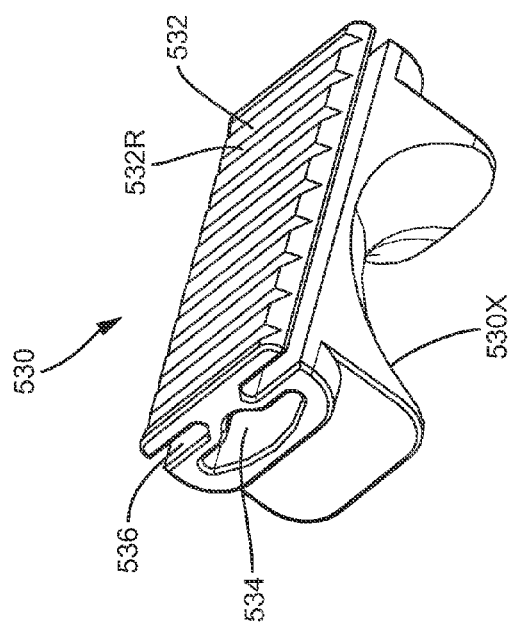

ANCHORING MECHANISM

FIELD OF INVENTION

The present invention is directed to systems or mechanisms for affixing material to bone.

BACKGROUND

The present disclosure is related to commonly owned and co-pending U.S. application Ser. No. 12/847,524, which has a filing date that is the same as the present disclosure, and which is hereby incorporated herein by reference in its entirety.

The present disclosure relates to mechanisms for affixing material to bone, and more particularly, systems for affixing at least a portion of material to a vertebral body.

SUMMARY OF THE INVENTION

A system for anchoring at least a portion of material to a vertebral body is disclosed. The anchoring system comprises a base configured to affix to the vertebral body and configured to receive the at least a portion of material, and an anchoring mechanism configured to engage with the base and configured to anchor the at least a portion of material, wherein the mechanism comprises at least one elastic element configured to apply pressure to the at least a portion of material so as to anchor the at least a portion of material to the base.

Also, a system for anchoring at least a portion of material to bone is disclosed. The system comprises a base configured to affix to the bone and configured to receive the at least a portion of material, and an anchoring mechanism configured to engage with the base and configured to anchor the at least a portion of material, wherein the mechanism comprises a mechanical spring configured to apply pressure to the at least a portion of material so as to anchor the at least a portion of material to the base.

Further, a method for attaching at least a portion of material to bone is disclosed. The method comprises placing the at least a portion of material into a first end of the base, and anchoring the at least a portion of material to the base by anchoring the at least a portion of material in an anchoring mechanism.

Additional aspects and features of the present disclosure will be apparent from the detailed description and claims as set forth below.

BRIEF DESCRIPTION OF THE DRAWINGS

FIG. 8 is an isometric view of another anchoring mechanism;

FIG. 8A is a top view of the anchoring mechanism of FIG. 8 in an unloaded state;

FIG. 8B is a top view of the anchoring mechanism of FIG. 8 in a loaded state;

DETAILED DESCRIPTION

Figure 1:
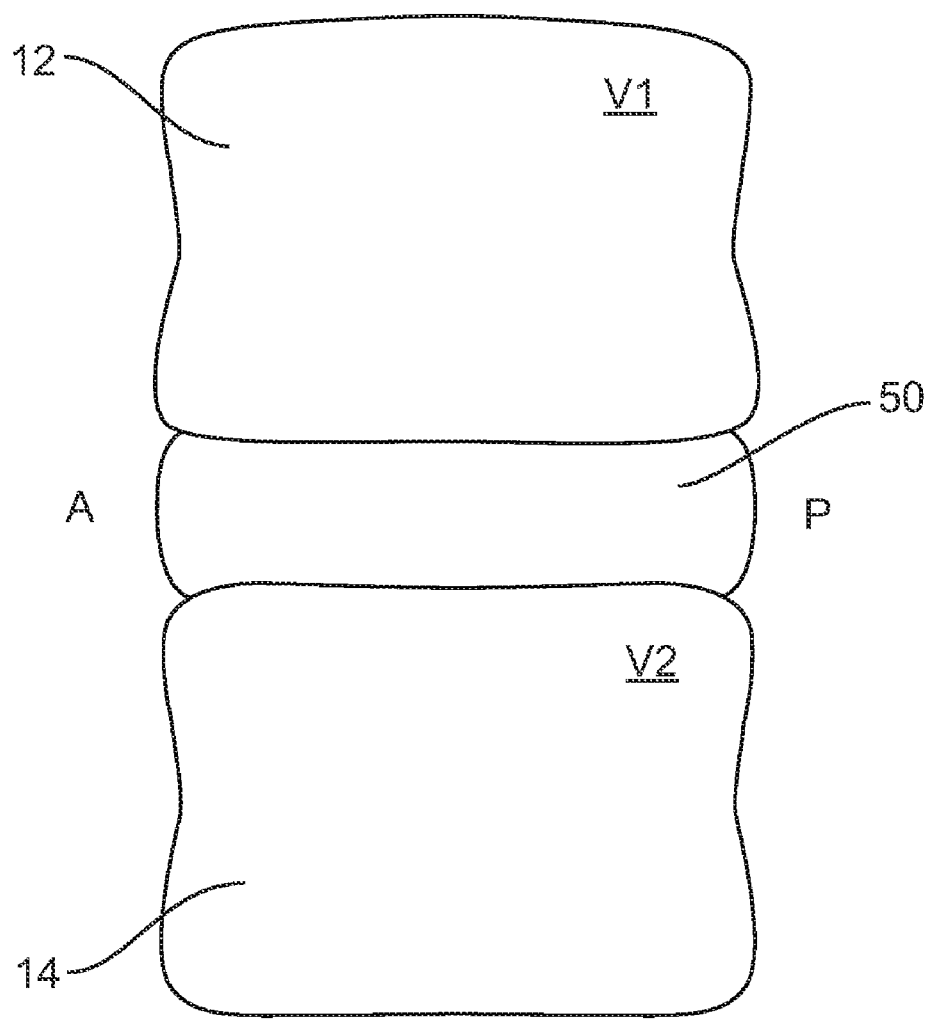
FIG. 1 is a schematic, cross-sectional view of two adjacent vertebral bodies.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows a schematic, cross-sectional view of two adjacent vertebral bodies V1 and V2 with an intervertebral disc 50 situated in its natural location between the two vertebral bodies V1 and V2. As shown in FIG. 1, vertebral body V1 represents a superior vertebral body and V2 represents an inferior vertebral body. Reference marker A represents an anterior side of the vertebral bodies V1 and V2, whereas reference marker P represents a posterior side of the vertebral bodies V1 and V2. As shown in FIG. 1, superior vertebral body V1 has a lateral surface 12 and inferior vertebral body V2 has a lateral surface 14.

Figure 2:
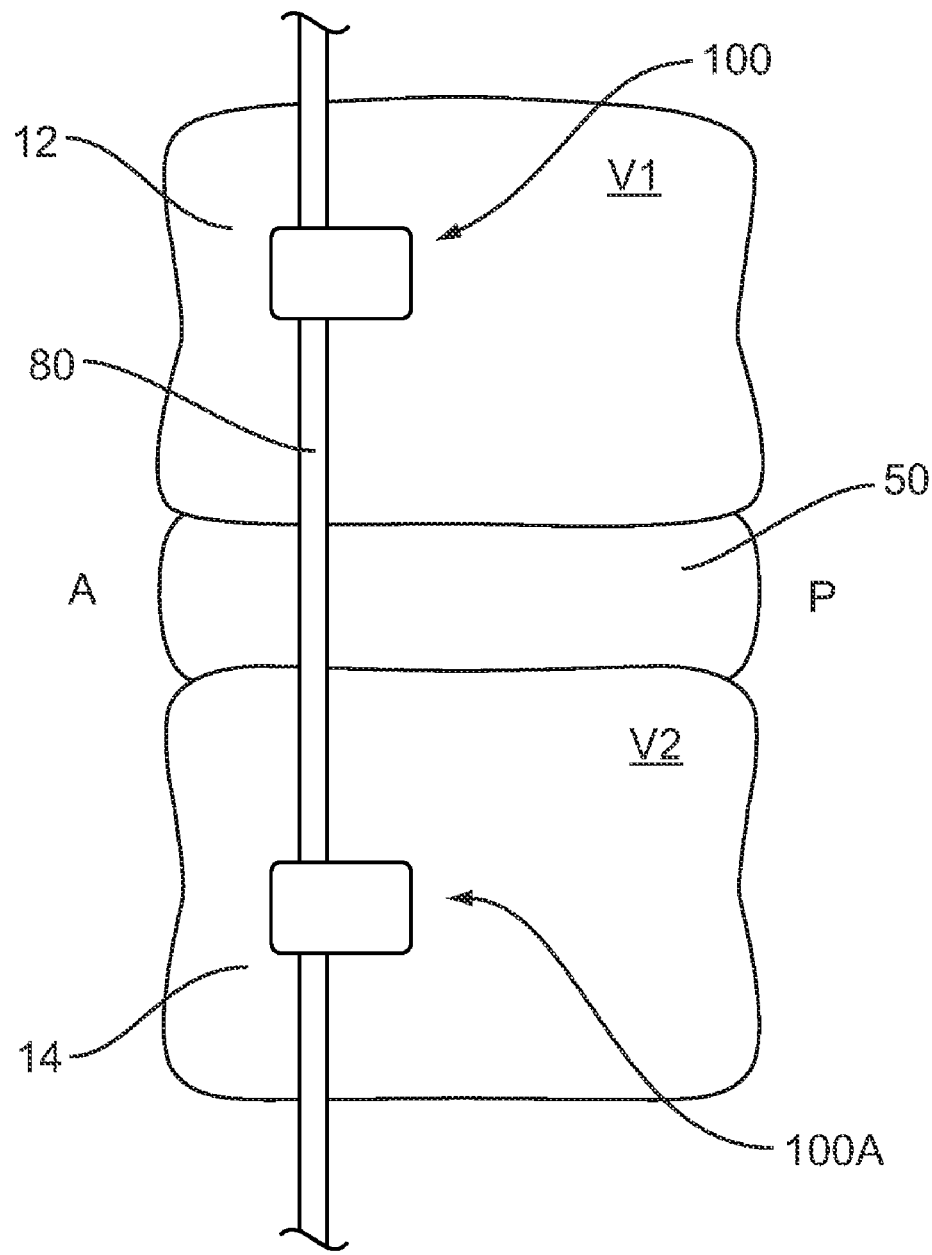
FIG. 2 is a schematic, side view of the vertebral bodies of FIG. 1 with an anchoring system.

FIG. 2 shows a schematic, side view of the vertebral bodies V1 and V2 of FIG. 1 with an anchoring system 100. The anchoring system 100 is used to anchor at least a portion of material 80 to a vertebral body V1 or V2. As show in FIG. 2, there is an anchoring system 100 affixed to the anterior lateral side of vertebral body V1 and an anchoring system 100A affixed to the anterior lateral side of vertebral body V2. The anchoring system 100 and/or 100A may be affixed to another location on the vertebral bodies V1 and V2, for example, they may be affixed to the pedicles (not shown) on the posterior section of the vertebral bodies V1 and V2.

Figure 3:
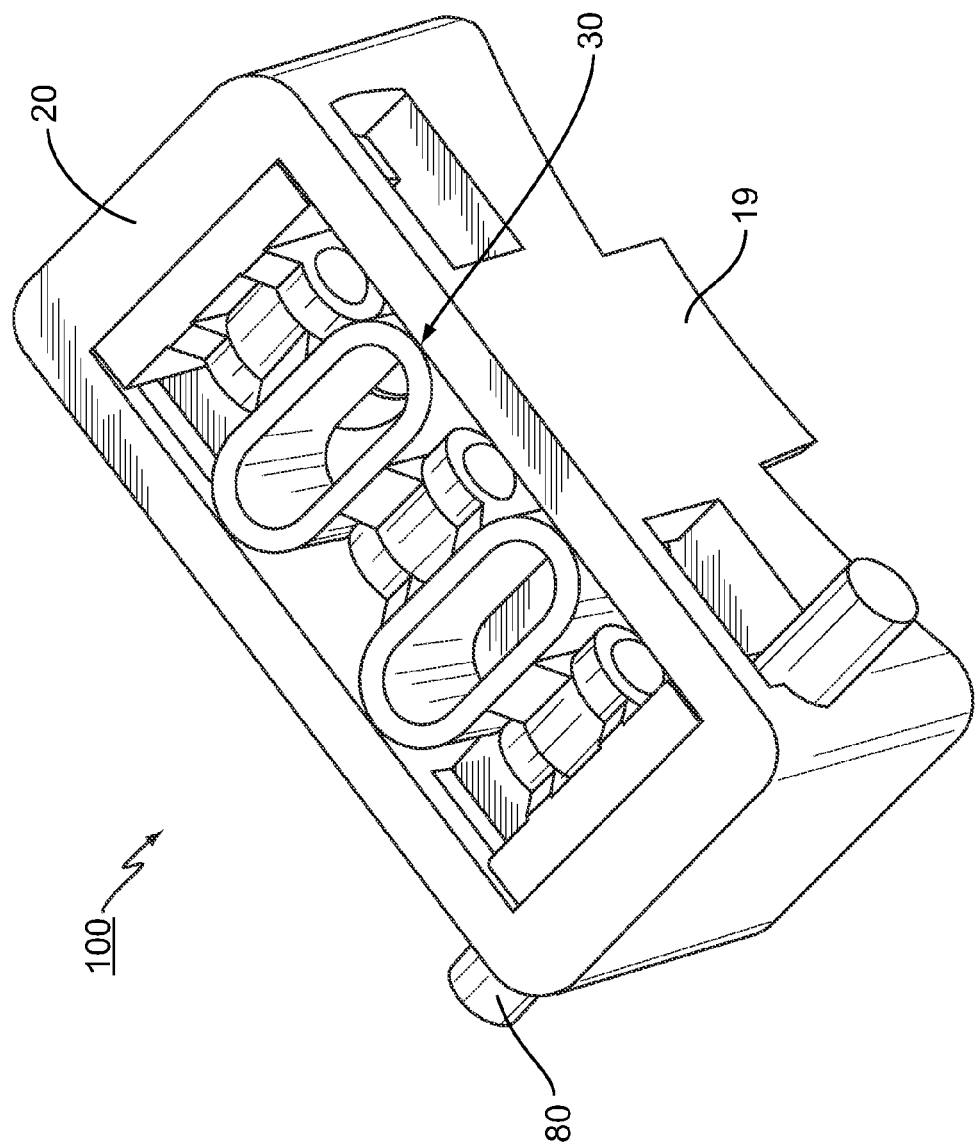
FIG. 3 is an isometric view of an anchoring system.

FIG. 3 shows an isometric view of an anchoring system 100. As shown in FIG. 3, the anchoring system 100 comprises a base 20 and an anchoring mechanism 30. The base 20 is configured to affix to the vertebral body V1 or V2 and configured to receive the at least a portion of material 80. The anchoring mechanism 30 is configured to engage with the base 20 and configured to anchor the at least a portion of material 80 to the base 20, wherein the mechanism 30 comprises at least one elastic element configured to apply pressure to the at least a portion of material 80 so as to anchor the at least a portion of material 80 to the base 20. Further, as shown in FIG. 3, the underside of the base 20 may have structures 19 such as anchors, keels, spikes, pegs, prongs, or similar structures to help affix the base 20 to the vertebral body V1 or V2.

Figure 4:
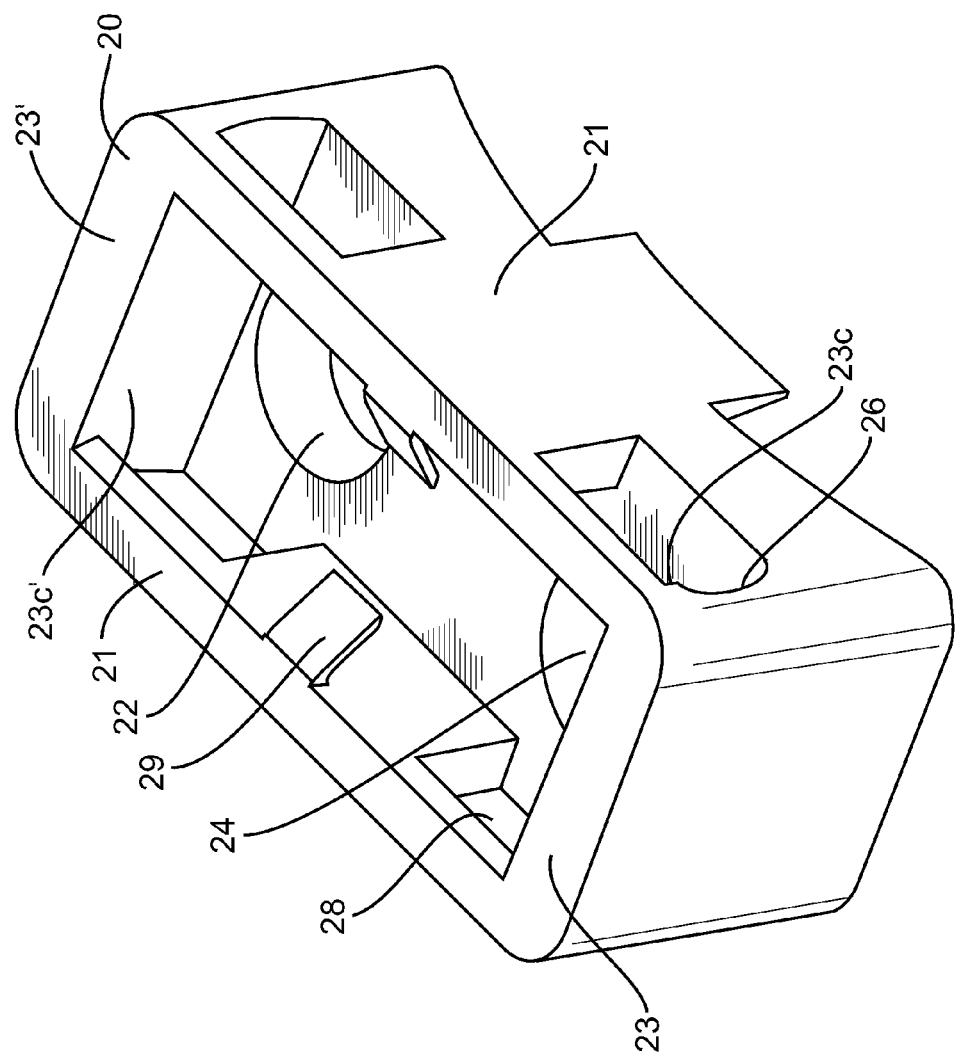
FIG. 4 is an isometric view of a base of the anchoring system of FIG. 3.

FIG. 4 shows an isometric view of the base 20 of the anchoring system 100 of FIG. 3. As shown in FIG. 4, the base 20 comprises two holes 22 and 24 for receiving fasteners (not shown) for affixing the base 20 to the vertebral body V1 or V2. The base 20 further comprises sidewalls 21 having slots 28. In addition, the inside surfaces 23c and 23c' of walls 23 and 23', respectively, of the base 20 may be concave to, for example, accommodate the at least a portion of material 80. Further, the slots 28 and corresponding portions of the walls 23 or 23' may have a recess 26 for accommodating at least a portion of the at least a portion of material 80. The base 20 further comprises a locking component 29 to help maintain pressure on the at least a portion of material 80. In doing so, the locking component 29 will help prevent disengagement of the anchoring mechanism 30.

Figure 5:
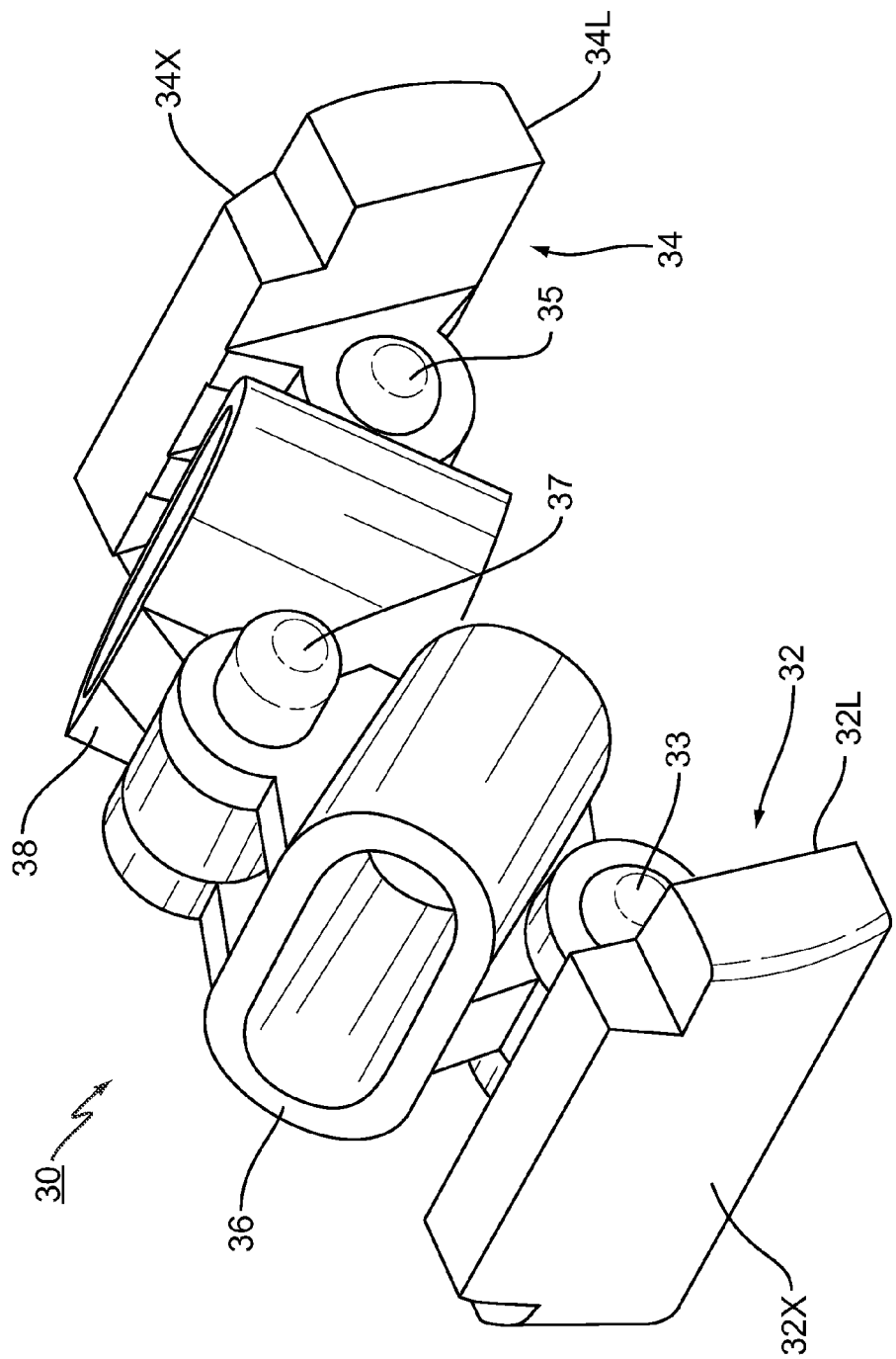
FIG. 5 is an isometric view of an anchoring mechanism of the anchoring system of FIG. 3.

FIG. 5 shows an isometric view of the anchoring mechanism of the anchoring system 100 of FIG. 3. As shown in FIG. 5, anchoring mechanism 30 comprises a first end component 32, a second end component 34, a first elastic element 36 and a second elastic element 38. As shown in FIG. 5, anchoring mechanism 30 further comprises a first end axle 33, a second end axle 35 and a center axle 37. As shown in FIG. 5, the first end axle 33 connects the first end component 32 to the first elastic element 36. As shown, the first end axle 33 allows the first end component 32 and the first elastic element 36 to rotate with respect to each other. In addition, as shown in FIG. 5, the second end axle 35 connects the second end component 34 to the second elastic element 38. As shown, the second end axle 35 allows the second end component 34 and the second elastic element 38 to rotate with respect to each other. Further, as shown in FIG. 5, the center axle 37 connects the first elastic element 36 to the second elastic element 38. As shown, the center axle 37 allows the first elastic element 36 and the second elastic element 38 to rotate with respect to each other.

As shown in FIG. 5, each of the first elastic element 36 and the second elastic element 38 are springs. More specifically, as shown, each of the first elastic element 36 and the second elastic element 38 are springs are mechanical springs. More specifically, as shown, each of the first elastic element 36 and the second elastic element 38 are compression springs. As shown, elastic elements 36 and 38 reduce in size when exposed to a compressive load. Note that although elastic elements 36 and 38 may operate in a desired "elastic" range, elastic elements 36 and 38 may be configured to experience at least some level of plastic deformation.

In operation, the base 20 of the anchoring system 100 will be affixed to a vertebral body, for example, V1 or V2, by placing fasteners such as screws through the holes 22 and 24 and into the vertebral body. After the base 20 is affixed to a vertebral body, the at least a portion of material 80 such as a tether is placed within the base as shown in FIG. 3. As shown in FIG. 3, the at least a portion of material 80 may be placed against the concave surface 23c and/or at least partially in the recess 26 of the base 20.

After the at least a portion of material 80 is in position within the base 20, the anchoring mechanism 30 is placed within the base 20. The anchoring mechanism 30 is first placed in the position as shown in FIG. 5. That is, as shown in FIG. 5, the longitudinal length of the anchoring mechanism 30 has a reduced-length. The longitudinal length of the anchoring mechanism 30 may be measured, for example, by the distance from the first end component 32 to the second end component 34. In shortening the distance between the first end component 32 to the second end component 34, the first elastic element 36 and the second elastic element 38 are rotated upward about center axle 37, the first elastic element 36 rotates with respect to the first end component 32 by rotating about the first end axle 33, and the second elastic element 38 rotates with respect to the second end component 34 by rotating about the second end axle 35. The resulting reduced-length anchoring mechanism 30, as shown in FIG. 5, allows for the anchoring mechanism 30 to be inserted into the base 20.

FIG. 3 shows the anchoring mechanism 30 after it is inserted into the base 20. Specifically, after the reduced-length anchoring mechanism 30 (as shown in FIG. 5) is placed into the base 20, the anchoring mechanism 30 is extended so as to increase the distance between the first end component 32 to the second end component 34. In the process of extending, the first elastic element 36 and the second elastic element 38 are rotated downward about center axle 37, the first elastic element 36 rotates with respect to the first end component 32 by rotating about the first end axle 33, and the second elastic element 38 rotates with respect to the second end component 34 by rotating about the second end axle 35. Thus, in the extended state of the anchoring mechanism 30, as shown in FIG. 3, the first elastic element 36 and the second elastic element 38 are each in compression. Because the elastic elements 36 and 38 are in compression, the first end component 32 imparts a force against a wall of the base 20 and a force against the at least a portion of material 80, thereby maintaining the at least a portion of material 80 in place. Similarly, the second end component 34 imparts a force against the opposite wall of the base 20. Specifically, surface 32X of the first end component 32 contacts the at least a portion of material 80 and the wall 23 of the base 20. Similarly, surface 34X of the second end component 34 contacts the wall 23' of the base 20. Surfaces 32X and 34X of the first and second end components 32 and 34, respectively, may be textured so as to improve their respective grips on the walls 23 and 23' and/or the at least a portion of material 80.

Note that the anchoring mechanism 30 may be contained within the base 20 (figure now shown) during the process of anchoring. That is, as shown in FIG. 5, the first end component 32 has sides 32L and the second end component 34 has sides 34L. Further, as shown in FIG. 4, the base 20 has walls 21 that have cut-outs 28. The sides 32L and 34L of the first end component 32 and the second end component 34, respectively, may be placed in the cut-outs 28 in walls 21 so that the anchoring mechanism 30 is contained in the base 20. In this way, the length of the anchoring mechanism 30 may be reduced and/or extended while the anchoring mechanism is contained in the base 20.

Further, once the length of anchoring mechanism 30 is extended, as shown in FIG. 3, locking component 29 may be used to help maintain pressure on the at least a portion of material 80. That is, when the length of anchoring mechanism 30 is extended, as shown in FIG. 3, because the elastic elements 36 and 38 are compressed, the anchoring mechanism 30 may have difficulty remaining in the base 20. That is, the compression forces of the elastic elements 36 and 38 may cause the various components of the anchoring mechanism 30 to rotate about the various axles 33, 35 and 37, causing the first end component 32 and the second end component 34 to lose contact with the walls 23 and 23' of the base 20. Consequently, once the length of anchoring mechanism 30 is extended in the base 20, the locking component 29 may engage axle 37 of anchoring mechanism 30 and prevent the various components of the anchoring mechanism 30 from rotating about the various axles 33, 35 and 37. In doing so, locking component 29 may help the first end component 32 and the second end component 34 keep contact with the walls 23 and 23' of the base 20, and thereby, help the anchoring mechanism 30 maintain pressure on the at least a portion of material 80.

Note that FIG. 5 shows one embodiment of an anchoring mechanism 30. That is, an anchoring mechanism 30 may comprise various arrangements of elastic elements. Further, note that instead of or in addition to the elastic elements 36 and 38 shown in the figures, one or more of the axles 33, 35 or 37 may contain a spring or elastic feature. In addition, an anchoring mechanism may comprise a single elastic element. For example, the anchoring mechanism 30 of FIG. 5 may have a single elastic element if one of the elastic elements 36 or 38 is not elastic. In addition, a single elastic element may be used when, for example, the base 20 is shorter in length. A base 20 of shorter length may be used when, for example, the base 20 has only one hole for receiving a fastener, which is configured for affixing the base 20 to the vertebral body V1 or V2.

Figure 6:
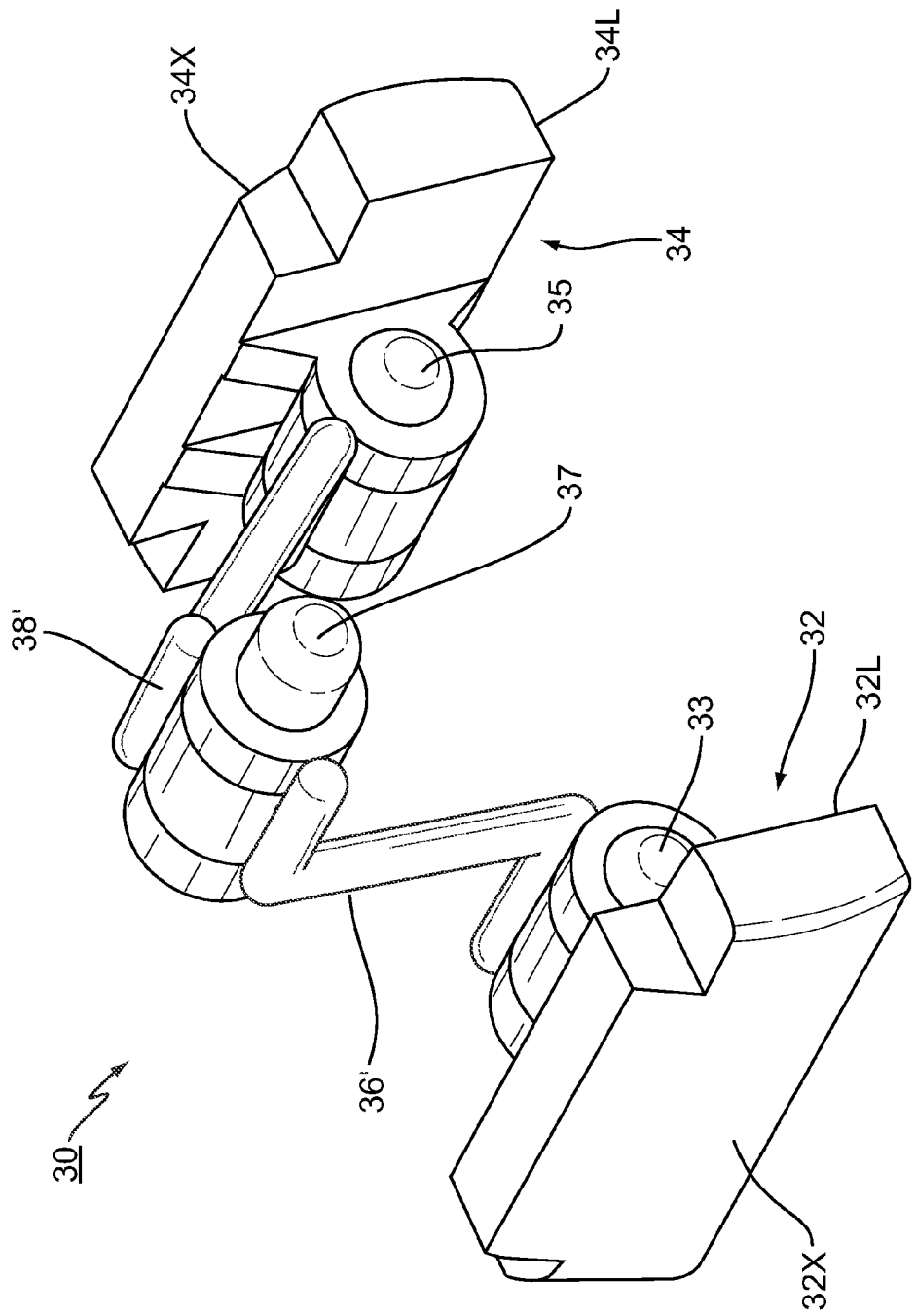
FIG. 6 is an isometric view of another anchoring mechanism.

FIG. 6 shows an isometric view of an example of an anchoring mechanism 30' that is different from that shown in FIG. 5. That is, the anchoring system of FIG. 6 has different elastic elements 36' and 38'. Specifically, where elastic elements 36 and 38 have open areas inside the elements (that is, the general shape of a circle or "O") which allow them to compress, elastic elements 36' and 38' have a general shape of a "Z" to allow them to compress.

The at least a portion of material 80 is non-rigid, and may be flexible. Further, as stated, the at least a portion of material 80 may be a tether or part of a tether that connects the anchoring system 100 to something else, for example, to another anchoring system on an adjacent vertebral body. Such a system is shown in FIG. 2. The at least a portion of material 80 may be any one or combination of a cloth, metal, solid polymer, fabric, mesh, or other biocompatible material. Some polymer materials may include but not be limited to, any one or combination of polyethylene, polyester, polyvinyl, polyvinyl alcohol, polyacrylonitrile, polyamide, polytetrafluoroethylene, poly-paraphenylene and terephthalamide. Further, the at least a portion of material 80 may be made of a suture wire of polyester or polyethylene. In addition, the at least a portion of material 80 may be elastic, woven, knitted, braided or flexible. Some woven, knitted or braided materials may, for example, include nylon, Dacron®, and/or woven fibers or filaments of polyester, polyethelene, polypropylene, polyetheretherketone ("PEEK"), polytetrafluoroethylene ("PTFE"), and/or woven PEEK. Some elastic materials may, for example, include latex, rubber, silicone, polyurethane, silicone-polyurethane copolymers, and/or polyolefin rubbers. Other suitable materials may, for example, include Gore-Tex®, Kevlar®, Spectra, polyether, polycarbonate urethane, shape memory material with pseudo elastic or superelastic characteristics, metals, metal alloys, and polymers, braided polymers, synthetic resorbable materials such as polyactide, polygycolide, polyorthoester, calcium phosphate, and/or glass, nonresorbable polyethylene, cellulose, materials that are potentially absorbable, and/or materials that are used in making artificial ligaments. Further, suitable materials should be non-biodegradable and non-resorbable. In addition to woven, braided, or knitted structures, the at least a portion of material 80 also may be composed of non-woven structures such as non-woven mesh or chained structures.

Figure 7:
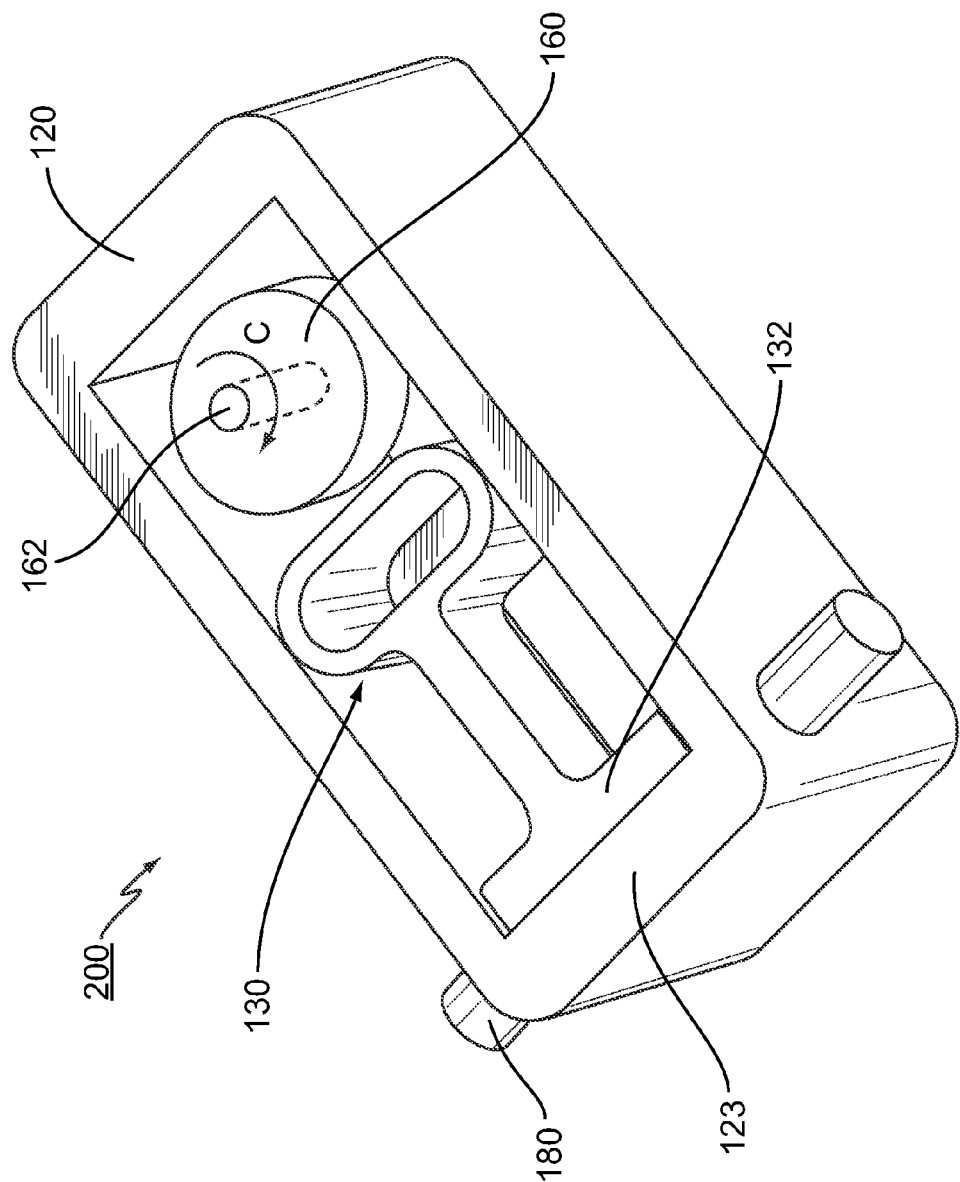
FIG. 7 is an isometric view of another anchoring system.

FIG. 7 shows an isometric view of another anchoring system 200. As shown in FIG. 7, the anchoring system 200 comprises a base 120 and an anchoring mechanism 130. The base 220 is configured to affix to the vertebral body V1 or V2, for example, in a manner similar to those described above, and configured to receive the at least a portion of material 180. The anchoring mechanism 130 is configured to engage with the base 120 and configured to anchor the at least a portion of material 180 to the base 120, wherein the mechanism 130 comprises at least one elastic element 130 configured to apply pressure to the at least a portion of material 180 so as to anchor the at least a portion of material 180 to the base 120. As shown in FIG. 7, anchoring system 200 further comprises a cam 160 that rotates around axle 162. Note that, as shown in FIG. 7, the cam 160 is not centrally located about the axle 162, but the axle 162 is offset from the center of the cam 160. As shown in FIG. 7, the elastic element 130 is engaged when the cam 160 is rotated, for example, in the direction shown as C (which is shown as clockwise). When the cam 160 is rotated in direction C, a force is applied against elastic member 130, which in turn, applies pressure to the at least a portion of material 180, which is situated between wall 123 of base 120 and wall 132 of elastic element 132.

FIG. 8 shows an isometric view of an anchoring mechanism 530 that may be used, for example, with the anchoring system 100 of FIG. 3. As shown in FIG. 8, the anchoring mechanism 530 is an elastic element 530. With reference to FIG. 5, the elastic element 530 may be used, for example, to replace the first end component 32 and the first elastic element 36, wherein a rigid element (not shown) may be connected to axle 37. In such an example, elastic element 530 has a first surface 530X that is configured for engaging the rigid element and a second surface 532 that is configured for engaging the at least a portion of material 80. As shown in the embodiment of FIG. 8, for example, surfaces 532 and 530X are rigid and substantially do not deform during use. Elastic element 530 comprises at least one pocket of air 534. Also, as shown, the elastic element 530 of FIG. 31 comprises additional areas of air 536 (shown as recesses in FIG. 8). As shown in the embodiment of FIG. 8, for example, areas 534 and 536 work together to provide movement of surface 532 toward surface 530X while the elastic element 530 experiences elastic deformation and, in some cases, experiences plastic deformation. When in its fully-inserted position on the base 20, the areas of air 536 are enclosed and may act in a similar fashion to the pocket of air 534. Areas of air (or "open" space") such as areas 534 and 536 help compress the elastic element 530 and apply pressure to the at least a portion of material 80 in a more uniform manner, thereby help maintaining the at least a portion of material 80 affixed to the base 20. As shown in the embodiment of FIG. 8, for example, the areas 534 and 536 may allow for compression of the elastic element 530 and apply pressure to the at least a portion of material 80 even if the elastic element 530 experiences some creep or other deformation and/or if at least a portion of material 80 experiences the same under load and/or after implantation. In addition, the second surface 532 of the elastic element 530 of FIG. 8 has a plurality of recesses 532R that help the second surface 532 engage the at least a portion of material 580.

FIG. 8A shows a top view of the anchoring mechanism 530 of FIG. 8 in an unloaded state. FIG. 8A shows another view of areas 534 and 536 and surfaces 530X and 532, and how each is oriented with respect to each other.

FIG. 8B shows a top view of the anchoring mechanism 530 of FIG. 8 in a loaded or compressed state. FIG. 8B shows another view of areas 534 and 536 and surfaces 530X and 532, and how each is oriented with respect to each other. As compared to FIG. 8A, FIG. 8B shows that the areas 534 and 536 have decreased in size.

Figure 11:
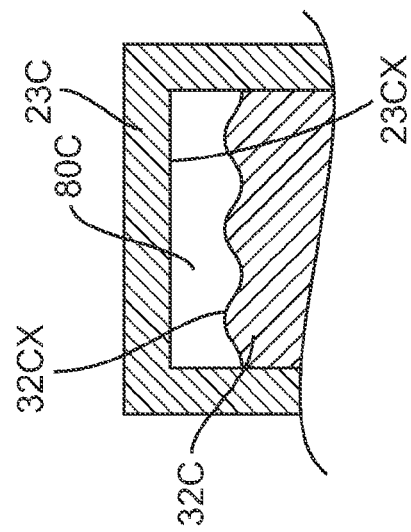
FIG. 11 is a top cross-sectional view of another area similar to that highlighted in FIG. 9.
Figure 10:
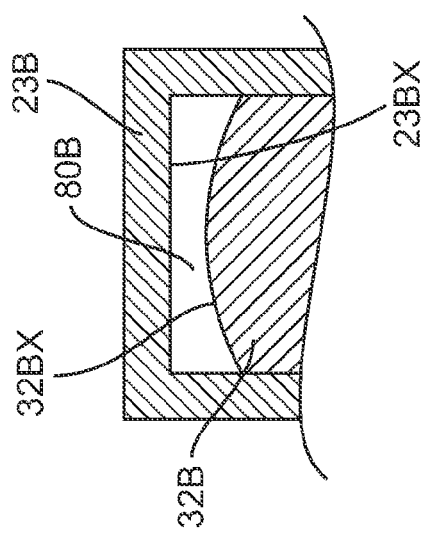
FIG. 10 is a top cross-sectional view of another area similar to that highlighted in FIG. 9.
Figure 9:
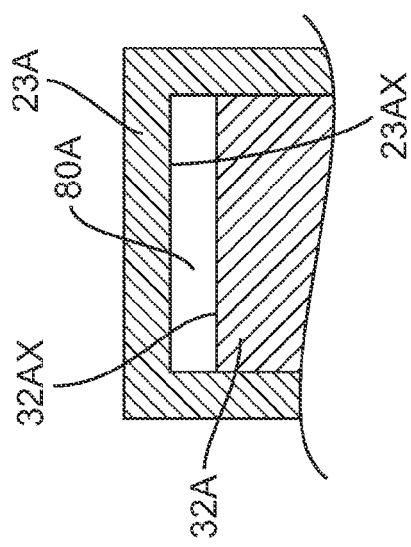
FIG. 9 is a top cross-sectional view of an area of where a first end component meets an inside surface.

FIG. 9 shows top cross-sectional view of the area of, for example, FIG. 3, where the first end component 32 meets inside surface 23. As shown in FIG. 9, the first end component is labeled 32A and the inside surface is labeled 23A. As shown in FIG. 9, surface 23AX is configured for receiving surface 32AX and the at least a portion of material 80. FIG. 10 shows a top cross-sectional view of another area similar to that highlighted in FIG. 9. Specifically, as shown in FIG. 10, surface 23BX of first end component 23B is configured for receiving surface 32BX of inside surface 32B and the at least a portion of material 80. FIG. 11 shows a top cross-sectional view of another area similar to that highlighted in FIG. 9.

Specifically, as shown in FIG. 11, surface 23CX of first end component 23C is configured for receiving surface 32CX of inside surface 32C and the at least a portion of material 80.

Note that the at least a portion of material 80 is not shown in FIGS. 9, 10 and 11, but it resides between the respective surfaces of the first end component and the inside surface, respectively. That is, as shown in FIG. 9, the at least a portion of material 80 is placed in the space and sandwiched between surface 23AX and surface 32AX, labeled as gap 80A. As shown in FIG. 10, the at least a portion of material 80 is placed in gap 80B. As shown in FIG. 11, the at least a portion of material 80 is placed in gap 80C. FIG. 9 shows an embodiment where surface 23AX of first end component 23A is substantially flat and where surface 32AX of inside surface 32A is substantially flat. FIG. 10 shows an embodiment where surface 23BX of first end component 2313 is substantially flat and where surface 32BX of inside surface 32B is substantially convexly curved. FIG. 11 shows an embodiment where surface 23CX of first end component 23C is substantially flat and where surface 32CX of inside surface 32C is substantially sinusoidal in shape (or having a shape of undulating or varying curvature). Where applicable, any of the surfaces shown in FIGS. 9-11, or any variation thereof or additional shapes, may be utilized for any surface designed to contact and anchor at least a portion of material, for example, 80 or 180. Specifically, certain profiles such as those shown in FIGS. 9-11 may improve the strength of retention of the at least a portion of material 80 and may reduce the potential for damage of the at least a portion of material 80 from stresses.

Figure 12:
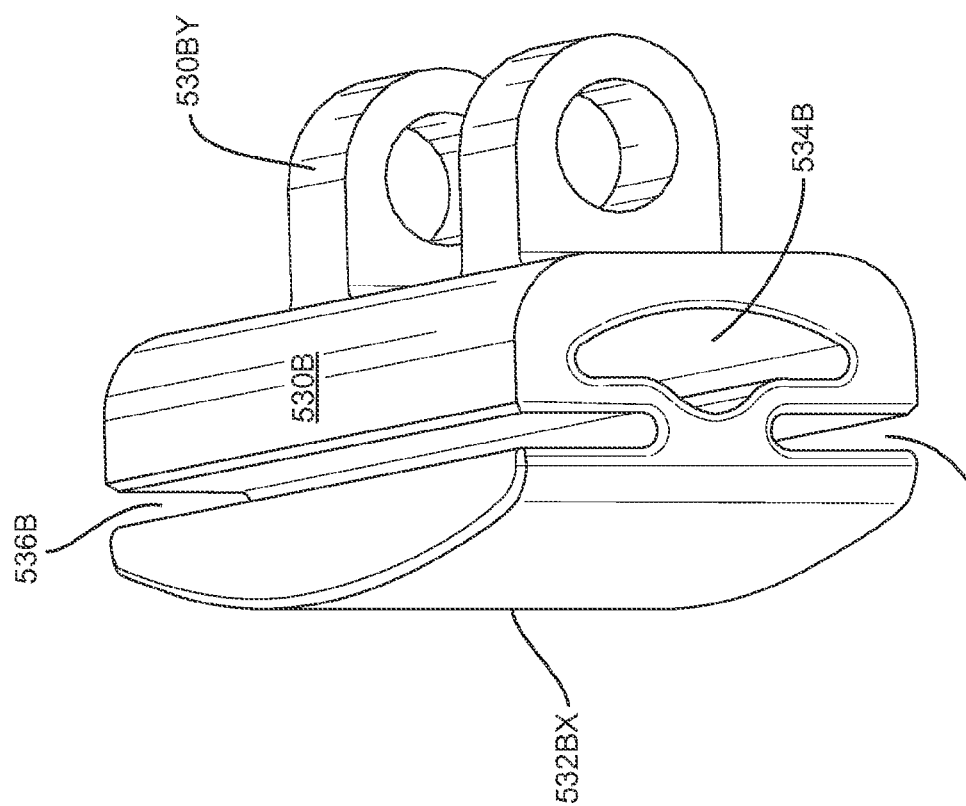
FIG. 12 is an isometric view of another anchoring mechanism.

FIG. 12 shows an isometric view of an anchoring mechanism 530B that may be used, for example, with the anchoring system 100 of FIG. 3. As shown in FIG. 12, the anchoring mechanism 530B is an elastic element 530B. With reference to FIG. 5, the elastic element 530B may be used, for example, to replace the first end component 32 and the first elastic element 36, wherein end portion 530BY may be connected to axle 37. Alternatively, elastic element 530B may be used, for example, to replace the first end component 32, wherein end portion 530BY may be connected to axle 33. In the embodiment shown in FIG. 12, elastic element 530 has first surface 530BY configured for engaging axle 33 or 37 and a second surface 532BX that is configured for engaging the at least a portion of material 80. As with elastic element 530, elastic element 530B comprises areas 534 and 536 so that elastic element 530B may operate in a fashion similar to that of elastic element 530. In addition, the second surface 532 of the elastic element 530 of FIG. 8 has a plurality of recesses 532R that help the second surface 532 engage the at least a portion of material 580. Also, as shown in FIG. 12, the anchoring mechanism 530B has a top sectional view that would be similar to that shown for the surface profiling shown in FIG. 10. Specifically, surface 532BX has a similar substantially convexly curved shape as does surface 32BX of FIG. 10.

Further, note that the various components of the anchoring system 100 or 200 may be made of a variety of materials and any combination thereof. Suitable materials for any component other than the at least a portion of material 80 or 180 include but are not limited to, any one or any combination of a metal, polymer, ceramic, or other biocompatible material. Except for the elastic elements, the components should be rigid. While the elastic components are elastic, they may be non-rigid. Even though the elastic elements may be mechanical springs, the elastic elements may not be mechanical springs. For example, suitable materials for the elastic elements may, for example, include latex, rubber, silicone, polyurethane, silicone-polyurethane copolymers, and/or polyolefin rubbers.

The terms "general" (or "generally") or "substantially" (or "substantial") as used herein may be applied to modify any quantitative representation which could permissibly vary without resulting in a change in the basic function to which it is related. For example, while the elastic elements 36 and 38 have the general shape of a circle or "O," it may be an elongated "O" (similar to a racetrack) or other shape that allows them to compress and provide the function of the elastic elements as described herein.

All adjustments and alternatives described above are intended to be included within the scope of the invention, as defined exclusively in the following claims. Those skilled in the art also should realize that such modifications and equivalent constructions or methods do not depart from the spirit and scope of the present disclosure, and that they may make various changes, substitutions, and alterations herein without departing from the spirit and scope of the present disclosure. For example, although the anchoring systems above are described as being configured to affix at least a portion of material to a vertebral body, they also may affix at least a portion of material to any bone. Similarly, although the anchoring systems are described as being configured to affix to an anterior and/or anterior lateral surface of a vertebral body, they also may affix to a posterior surface of a vertebral body (such as a pedicle), a lateral surface of a vertebral body or any plurality or combination of such surfaces.

Furthermore, as used herein, the terms components and elements may be interchanged. It is understood that all spatial references, such as "superior," "inferior," "anterior," "posterior," "above," "lower," "outside," "inside," "higher," "lower," "outer," "inner," "extended," "reduced," "shorter," "longer," and "perimeter" are for illustrative purposes and can be varied within the scope of the disclosure.

The invention claimed is:

1. A system for anchoring at least a portion of material to a vertebral body, the system comprising:
   a base configured to affix to the vertebral body and configured to receive the at least a portion of material;
   an anchoring mechanism configured to engage with the base and configured to anchor the at least a portion of material, the anchoring mechanism comprising:
   a first end component;
   a second end component;
   a first elastic element connected to the first end component;
   a second elastic element connected to the second end component;
   a first end axle connects to the first end component to the first elastic element configured to allow the first end component and the first elastic element to rotate with respect to each other;
   a second end axle connects to the second end component to the second elastic element configured to allow the second end component and the second elastic element to rotate with respect to each other; and
   a center axle connects to the first elastic element to the second elastic element configured to allow the first elastic element and the second elastic element to rotate with respect to each other to apply a force to the at least a portion of material,
   wherein at least one of the first or second elastic elements is configured to apply pressure to the at least a portion of material so as to anchor the at least a portion of material to the base.

2. The system of claim 1, wherein the at least one elastic element is a spring.

3. The system of claim 2, wherein the spring is a mechanical spring.

4. The system of claim 3, wherein the mechanical spring is a compression spring.

5. The system of claim 1, further comprising the at least a portion of material.

6. The system of claim 5, wherein the at least a portion of material is non-rigid.

7. The system of claim 5, wherein the at least a portion of material is flexible.

8. The system of claim 5, wherein the at least a portion of material is part of a tether.

9. The system of claim 1, wherein the base comprises two holes for receiving fasteners for affixing the base to the vertebral body.

10. The system of claim 1, wherein the base comprises a locking component to help maintain pressure on the at least a portion of material.

11. A system for anchoring at least a portion of material to bone, the system comprising:
    a base configured to affix to the bone and configured to receive the at least a portion of material;
    an anchoring mechanism configured to engage with the base and configured to anchor the at least a portion of material, the anchoring mechanism comprising:
    a first end component;
    a second end component;
    a first spring element connected to the first end component;
    a second spring element connected to the second end component;
    a first end axle connects to the first end component to the first elastic element configured to allow the first end component and the first elastic element to rotate with respect to each other;
    a second end axle connects to the second end component to the second elastic element configured to allow the second end component and the second elastic element to rotate with respect to each other; and
    a center axle connects to the first elastic element to the second elastic element configured to allow the first elastic element and the second elastic element to rotate with respect to each other to apply a force to the at least a portion of material,
    wherein at least one of the first or second spring elements is configured to apply pressure to the at least a portion of material so as to anchor the at least a portion of material to the base.

12. The system of claim 11, further comprising the at least a portion of material.

13. The system of claim 12, wherein the at least a portion of material is flexible.

14. The system of claim 11, wherein the base comprises two holes for receiving fasteners for affixing the base to the bone.

15. The system of claim 11, wherein the base comprises one hole for receiving a fastener for affixing the base to the bone.

16. The system of claim 11, further comprising the at least a portion of material.

17. The system of claim 16, wherein the at least a portion of material is flexible.

18. The system of claim 17, wherein the at least a portion of material is part of a tether.

19. A method for attaching at least a portion of material to bone comprising:
    attaching a base to bone;
    placing the at least a portion of material into a first end of the base; and
    anchoring the at least a portion of material to the base by anchoring the at least a
    portion of material in an anchoring mechanism, the anchoring mechanism comprising:
    a first end component;
    a second end component;
    a first elastic element connected to the first end component;
    a second elastic element connected to the second end component;
    a first end axle connects to the first end component to the first elastic element configured to allow the first end component and the first elastic element to rotate with respect to each other;
    a second end axle connects to the second end component to the second elastic element configured to allow the second end component and the second elastic element to rotate with respect to each other; and
    a center axle connects to the first elastic element to the second elastic element configured to allow the first elastic element and the second elastic element to rotate with respect to each other to apply a force to the at least a portion of material.

20. The method of claim 19, wherein the step of anchoring comprises:
    placing the at least a portion of material within the base so as to be engaged by a elastic element within the base; and
    engaging the elastic element such pressure is applied to the at least a portion of material.

* * * * *